United States Patent
Hamrock

(10) Patent No.: US 6,683,209 B2
(45) Date of Patent: Jan. 27, 2004

(54) AROMATIC IMIDE AND AROMATIC METHYLIDYNETRISSULFONYL COMPOUNDS AND METHOD OF MAKING

(75) Inventor: Steven Joseph Hamrock, Stillwater, MN (US)

(73) Assignee: 3M Innovative Properties Company, Saint Paul, MN (US)

(*) Notice: Subject to any disclaimer, the term of this patent is extended or adjusted under 35 U.S.C. 154(b) by 0 days.

(21) Appl. No.: 10/436,325

(22) Filed: May 12, 2003

(65) Prior Publication Data

US 2003/0208006 A1 Nov. 6, 2003

Related U.S. Application Data

(62) Division of application No. 10/042,024, filed on Oct. 25, 2001.

(51) Int. Cl.[7] ............... C07C 317/14; C07C 311/37; C08F 8/34
(52) U.S. Cl. ............... 564/84; 562/11; 562/12; 562/65; 562/430; 525/333.5; 568/28
(58) Field of Search ............... 562/11, 12, 65, 562/430; 564/84; 525/333.5; 568/28

(56) References Cited

U.S. PATENT DOCUMENTS

| | | | |
|---|---|---|---|
| 3,546,180 A | 12/1970 | Caldwell et al. | 260/76 |
| 4,505,997 A | 3/1985 | Armand et al. | 429/192 |
| 4,758,498 A | 7/1988 | Harada et al. | 430/216 |
| 5,072,040 A | 12/1991 | Armand | 564/82 |
| 5,273,840 A | 12/1993 | Dominey | 429/192 |
| 5,463,005 A | 10/1995 | Desmarteau | 526/240 |
| 5,514,493 A | 5/1996 | Waddell et al. | 429/199 |
| 5,652,072 A | 7/1997 | Lamanna et al. | 429/198 |
| 5,827,602 A | 10/1998 | Koch et al. | 429/194 |
| 5,879,828 A | 3/1999 | Debe et al. | 429/41 |
| 5,965,054 A | 10/1999 | McEwen et al. | 252/62.2 |
| 6,063,522 A | 5/2000 | Hamrock et al. | 429/200 |
| 6,090,895 A | 7/2000 | Mao et al. | 525/330.9 |

FOREIGN PATENT DOCUMENTS

GB 1281736 7/1972

OTHER PUBLICATIONS

Argyropoulos, D., and Lenk, R. S., *Condensation Products from Imidobis(sulfuryl Chloride)* Journal of Applied Polymer Science, vol. 26, (1981), pp. 3073–3084.

Roesky, Von H. W., and Giere, H. H., *Darstellung von N–Trifluoromethansulfonyl–sulfonylfluoridamid und einige reaktionen*[1], Inorg. Nucl. Chem. Letters, vol. 7, pp. 171–175, (1971) Pergannon Press.

Becke–Goehring & Fluck; *Imidodisulfuric Acid Chloride*, Inorganic Syntheses, vol. VIII, (1966), pp. 105–107.

Doyle, M., Choi, S. K., and Proulx, G., *High–Temperature Proton Conducting Membranes Based on Perfluorinated Ionomer Membrane–Ionic Liquid Composites*, Journal of the Electrochemical Society, 147, (1), (2000).pp. 34–37.

*Primary Examiner*—Peter O'Sullivan
(74) *Attorney, Agent, or Firm*—Philip Y. Dahl

(57) ABSTRACT

A method is provided for making aromatic-imide and aromatic-methylidynetrissulfonyl species by reaction of aromatic species with a reactant according to formula (I):

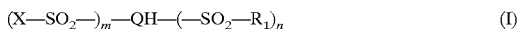

$$(X{-}SO_2{-})_m{-}QH{-}({-}SO_2{-}R_1)_n \qquad (I)$$

wherein Q is C or N; wherein each X is independently selected from the group consisting of halogens, typically F or Cl; wherein each $R_1$ is independently selected from the group consisting of aliphatic and aromatic groups, which may or may not be saturated, unsaturated, straight-chain, branched, cyclic, heteroatomic, polymeric, halogenated, fluorinated or substituted; wherein m is greater than 0; wherein m+n=2 when Q is N; and wherein m+n=3 when Q is C. Ar may be derived from an aromatic polymeric compound. In addition, compounds are provided according to the formula: $(Ar{-}SO_2{-})_m{-}QH{-}({-}SO_2{-}R_1)_n$ wherein $R_1$ comprises a highly acidic group selected from sulfonic acid, carboxylic acid and phosphonic acid, and Ar is derived from an aromatic compound.

4 Claims, No Drawings

AROMATIC IMIDE AND AROMATIC METHYLIDYNETRISSULFONYL COMPOUNDS AND METHOD OF MAKING

Cross Reference to Related Application

This application is a divisional of U.S. Ser. No. 10/042,024, filed Oct. 25, 2001, now allowed, the disclosure of which is herein incorporated by reference.

FIELD OF THE INVENTION

This invention relates to the synthesis of aromatic-imide and aromatic-methylidynetrissulfonyl species. The synthesis proceeds by reaction of aromatic species, including aromatic polymers, with a reactant according to the formula: $(X-SO_2-)_m-QH-(-SO_2-R_1)_n$; wherein Q is C or N and X is a halogen. The present invention additionally relates to compounds according to the formula: $(Ar-SO_2-)_m-QH-(-SO_2-R_1)_n$ wherein $R_1$ comprises a highly acidic group selected from sulfonic acid, carboxylic acid and phosphonic acid, which may be particularly useful as electrolytes.

BACKGROUND OF THE INVENTION

U.S. Pat No. 6,090,895 discloses crosslinked polymers having imide crosslinking groups and methods of crosslinking polymers to form imide crosslinking groups. These crosslinked polymers may be useful as polymer electrolyte membranes (PEM's) in fuel cells. The reference discloses methods of making imides by reaction of acid halides with amides, including aromatic acid halides and aromatic amides. The acid halides may be formed by haloacidification, e.g., chlorosulfonation, of aromatic species.

U.S. Pat No. 6,063,522 discloses electrolytes for use in electrochemical cells that include imide and methide conductive salts. The reference also discloses methods of making imides by reaction of acid halides with amides.

U.S. Pat. No. 4,505,997 discloses syntheses of imides by reaction of sulfonate and sulfonic anhydride species with urea. The reference discloses electrolytes comprising imide functional groups.

U.S. Pat. No. 5,652,072 discloses syntheses of imides by reaction of sulfonyl halide species with ammonia or with amide species. The reference discloses electrolytes comprising imide functional groups.

U.S. Pat. No. 5,072,040 discloses syntheses of imides by reaction of sulfonyl halide species with nitride species. The reference suggests the use of imide functional species in electrolytes.

U.S. Pat. No. 5,514,493 discloses syntheses of imides by reaction of sulfonyl halide species with ammonia or with amide species. The reference discloses electrolytes comprising imide functional groups.

U.S. Pat. No. 5,463,005 discloses perfluorinated monomers and polymers comprising sulfonyl and carbonyl imide groups for use as solid polymer electolytes. The reference discloses a synthesis of imides by reaction of amides with hexamethyldisilazine followed by reaction with a sulfonyl fluoride.

Argyropoulos & Lenk, "Condensation Products from Imidobis(sulfuryl Chloride)," *J. Ap. Polym. Sci.* v. 26, pp. 3073–3084 (1981), discloses reactions of imidobis(sulfuryl chloride).

SUMMARY OF THE INVENTION

Briefly, the present invention provides a method of making aromatic-imide and aromatic-methylidynetrissulfonyl species by reaction of aromatic species with a reactant according to formula (I):

$$(X-SO_2-)_m-QH-(-SO_2-R_1)_n \quad (I)$$

wherein Q is C or N; wherein each X is independently selected from the group consisting of halogens, typically F or Cl; wherein each $R_1$ is independently selected from the group consisting of aliphatic and aromatic groups, which may or may not be saturated, unsaturated, straight-chain, branched, cyclic, heteroatomic, polymeric, halogenated, fluorinated or substituted; wherein m is greater than 0; wherein m+n=2 when Q is N; and wherein in m+n=3 when Q is C. Ar may be derived from an aromatic polymeric compound.

In another aspect, the present invention concerns compounds according to formula (V), which compounds may be made using the method according to the present invention:

$$(Ar-SO_2-)_m-QH-(-SO_2-R_1)_n \quad (V)$$

wherein Ar is an aromatic group derived from an aromatic compound; wherein Q is C or N; wherein each $R_1$ is independently selected from the group consisting of aliphatic and aromatic groups, which may or may not be saturated, unsaturated, straight-chain, branched, cyclic, heteroatomic, polymeric, halogenated, fluorinated or substituted; wherein at least one $R_1$ contains at least one highly acidic group selected from sulfonic acid, carboxylic acid and phosphonic. acid; wherein m and N are each greater than 0; wherein m+n=2 when Q is N; and wherein m+n=3 when Q is C.

What has not been described in the art, and is provided by the present invention, is a simple method of synthesizing aromatic imides and aromatic methylidynetrissulfonyl species by direct substitution of aromatic species, including pre-existing aromatic polymers, by use of the reactants described herein.

In this application:

"highly acidic" means having a pKa<5;

"highly halogenated" means containing halogen in an amount of 40 wt % or more, but typically 50 wt % or more, and more typically 60 wt % or more; and "highly fluorinated" means containing fluorine in an amount of 40 wt % or more, but typically 50 wt % or more, and more typically 60 wt % or more; and "substituted" means, for a chemical species, substituted by conventional substituents which do not interfere with the desired product or process, e.g., substituents can be alkyl, alkoxy, aryl, phenyl, halo (F, Cl, Br, I) cyano, nitro, etc.

It is an advantage of the present invention to provide a simple and convenient synthetic route to aromatic-imide and aromatic-methylidynetrissulfonyl electrolytes, including solid polymer electrolytes, which are useful in electrochemical devices such as batteries and fuel cells.

DETAILED DESCRIPTION OF PREFERRED EMBODIMENTS

The present invention provides a method of making aromatic-imide and aromatic-methylidynetrissulfonyl species by reaction of aromatic species with a reactant according to formula (I):

$$(X-SO_2-)_m-QH-(-SO_2-R_1)_n \quad (I)$$

wherein Q is C or N; wherein each X is independently selected from the group consisting of halogens; wherein each $R_1$ is independently selected from the group consisting of wherein $R_1$ is selected from the group consisting of aliphatic and aromatic groups, which may or may not be saturated, unsaturated, straight-chain, branched, cyclic, heteroatomic, polymeric, halogenated, fluorinated or substituted; wherein m is greater than 0; wherein m+n=2 when Q is N; and wherein m+n=3 when Q is C.

For the reactant according to formula (I), Q may be C or N but is more typically N. Where Q is N, m may be 1 or 2. Where Q is C, m may be 1, 2 or 3, but is typically 1 or 2. Each X is a halogen, typically F or Cl, and most typically Cl.

$R_1$ is any suitable group that does not interfere with the synthesis according to the present invention and which provides a product having desired characteristics. Each R may be aromatic or aliphatic; may be saturated or unsaturated; maybe straight-chain, branched, or cyclic; may be heteroatomic or non-heteroatomic; may comprise a polymer; and may additionally be substituted including in particular halogenation, including in particular fluorination. $R_1$ typically comprises between 0 and 20 carbon atoms, more typically 0 to 8 carbon atoms, more typically 0 to 4 carbon atoms. Where the product species is intended for use as an electrolyte, $R_1$ is typically highly halogenated, more typically highly fluorinated, more typically perhalogenated, and most typically perfluorinated. Where the product species is intended for use as an electrolyte, $R_1$ is typically selected from: trihalomethyl, pentahaloethyl, heptahalopropyl, and nonahalobutyl, more typically where halogen substituents are selected from F and Cl. More typically, $R_1$ is selected from: trifluoromethyl, pentafluoroethyl, heptafluoropropyl, and nonafluorobutyl, most typically trifluoromethyl.

$R_1$ may advantageously contain additional highly acidic groups, typically including sulfonic acids, carboxylic acids and phosphonic acids, most typically sulfonic acid groups. $R_1$ may contain the highly acidic group according to formula (IV):

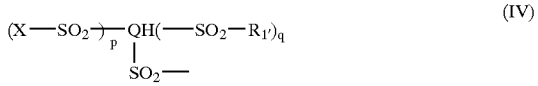

(IV)

wherein Q and X are as defined above, wherein $R_{1'}$ is selected from the same group as $R_1$ defined above except that $R_{1'}$ is typically not another group according to formula (IV), wherein p+q=1 when Q is N; and wherein p+q=2 when Q is C.

Alternately, $R_1$ may advantageously contain additional aromatic-binding groups such as sulfonyl halides or groups according to formula (IV) above where p>0. Where $R_1$ contains additional aromatic-binding groups and Ar is polymeric, crosslinking may result.

The reactant according to formula (I) above may be synthesized by methods such as described in Roesty & Giere, "Darstellung von N-Trifluormethanesulfonyl-sulfonylfluoridamid und einige reaktionen," *Inorg. Nucl. Chem.* v. 7, pp. 171–175 (1971) or Becke-Goehring & Fluck, "Imidodisulfuric acid chloride," *Inorganic Synthesis*, v. 8, pp. 105–107 (1966), which are incorporated by reference herein, or by methods analogous thereto, or by other methods known in the art.

Ar may be polymeric or non-polymeric. Polymeric examples of Ar include polymers with aromatic groups in the polymer backbone, such as polyphenylene oxide (PPO), and polymers with pendent aromatic groups, such as polystyrene. Aromatic polymers which may be useful as Ar in the present reaction include PPO, polystyrene, polyether ether ketone (PEEK), polyether ketone (PEK) and polysulfone and substituted derivatives thereof. Where m is greater than 1, a crosslinked product may result. Mixtures of reactants may be used to control the degree of crosslinking, such as mixtures of m=1 reactants and m=2 reactants.

Non-polymeric examples of Ar include aromatic groups having 5 to 20 carbon atoms, including monocyclic and polycyclic species and including heteroatomic and non-heteroatomic species. Additional aromatic species which may be useful as Ar in the present reaction include: benzene, toluene, naphthalene, anthracene, phenanthrene, fluorene, biphenyl, terphenyl, stillbene, indene, chrysene, pyrene, tetracene, fluoranthrene, coronene, pyridine, pyridazine, pyrimidine, pyrazine, imidazole, pyrazole thiazole, oxazole, triazole, quinoline, benzofuran, indole, benzothiophene, carbazole, and aromatic isomers and substituted derivatives thereof.

The aromatic reactant and the reactant according to formula (I) may be combined under any suitable reaction conditions. The reaction conditions are advantageously anhydrous. The reactants may be combined in solvent or neat. Where Ar is polymeric, the reactants are typically combined in an inert solvent such as $CCl_4$. Alternately, the reactant may be imbibed into the polymer, either neat or by use of a solvent. In this case, the polymer may be preformed into a membrane or other useful shape. The reaction mixture is typically heated. Catalyst may be added but is not necessary.

The method of the present invention may be used to make a class of aromatic-imide and aromatic-methylidynetrissulfonyl species bearing additional acidic functions which may be useful as electrolytes, according to formula (V):

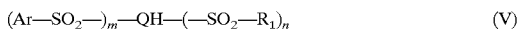

(V)

wherein Ar is an aromatic group derived from an aromatic compound; wherein Q is C or N; wherein each $R_1$ is independently selected from the group consisting of aliphatic and aromatic groups, which may or may not be saturated, unsaturated, straight-chain, branched, cyclic, heteroatomic, polymeric, halogenated, fluorinated or substituted; wherein at least one $R_1$ contains at least one additional highly acidic group; wherein m is greater than 0; wherein n is greater than 0; wherein m+n=2 when Q is N; and wherein m+n=3 when Q is C. Typically, Q is N, m=1 and n=1. Typically, the additional acid group of $R_1$ is selected from sulfonic acids, carboxylic acids, phosphonic acids, imides, and methylidynetrissulfonyl groups, most typically sulfonic acid groups. $R_1$ may advantageously comprise an aromatic group. $R_1$ may advantageously comprise an aromatic group according to the formula: $-PhY_{5-v}(SO_3H)_v$ where Ph is phenyl; each Y is independently selected from H, F, Cl and $CH_3$; and v is 1, 2 or 3, more typically 1 or 2, most typically 1.

Compounds according to formula (V) include those wherein Ar is derived from an aromatic polymeric compound. In one embodiment, Ar is an aromatic polymer bearing numerous pendent imide or methylidynetrissulfonyl groups according to formula (V). Suitable polymers may include polymers with aromatic groups in the polymer backbone, such as polyphenylene oxide (PPO), and polymers with pendent aromatic groups, such as polystyrene. Aromatic polymers which may be useful as Ar in the present reaction include PPO, polystyrene, polyether ether ketone (PEEK), polyether ketone (PEK) and polysulfone and substituted derivatives thereof.

This invention is useful in the synthesis of aromatic-imide and aromatic-methylidynetrissulfonyl electrolytes, including solid polymer electrolytes, which are useful in electrochemical devices such as batteries and fuel cells.

Objects and advantages of this invention are further illustrated by the following examples, but the particular materials and amounts thereof recited in these examples, as well as other conditions and details, should not be construed to unduly limit this invention.

EXAMPLES

Unless otherwise noted, all reagents were obtained or are available from Aldrich Chemical Co., Milwaukee, Wis., or may be synthesized by known methods.

EXAMPLE 1

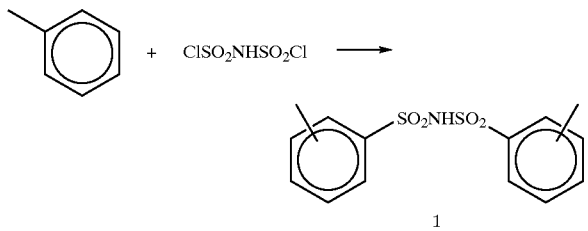

$(ClSO_2)_2NH$ (1 g) (synthesized according to Becke-Goehring & Fluck, "Imidodisulfuric acid chloride," *Inorganic Synthesis*, v. 8, pp. 105–107 (1966)) was mixed with 5 g of toluene and heated to 100° C. under nitrogen for 24 hours. The solution was then dried on a rotary evaporator to give an oily white solid. To this was added 5 ml of water and then 40 ml of 1 M LiOH. The resulting solution was stirred overnight and filtered, and evaporation of the solvent gave a white solid. This was stirred overnight with 100 ml of THF and filtered. Evaporation gave 2.10 g of a white solid identified by NMR as mixture of the ortho and para isomers of the lithium salt of the corresponding bis aromatic imide (compound 1).

EXAMPLE 2

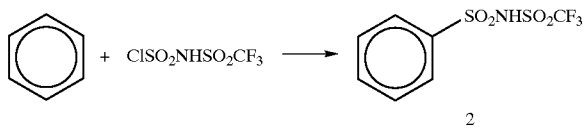

$CF_3SO_2NHSO_2Cl$ (0.86 g) (synthesized according to Roesty & Giere, "Darstellung von N-Trifluormethanesulfonyl-sulfonylfluoridamid und einige reaktionen," *Inorg. Nucl. Chem.* v. 7, pp. 171–175 (1971)) was dissolved in 5 g of benzene. The resulting solution was refluxed for 18 hours under nitrogen and the solvent was removed by vacuum. The remaining solid was mixed with 5 ml of 5 M LiOH and dried. The solids were then washed with 10 ml of THF, filtered and the THF was removed by vacuum to give a light yellow solid. NMR ($^1$H and $^{19}$F) showed this to be $CF_3SO_2-N^--SO_2(C_6H_5)$ Li$^+$, (Li salt of compound 2) along with smaller amounts of $CF_3SO_2NH_2$ and benzene sulfonate byproducts.

EXAMPLE 3

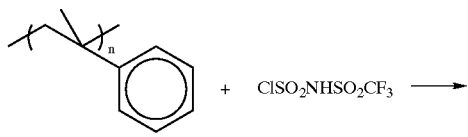

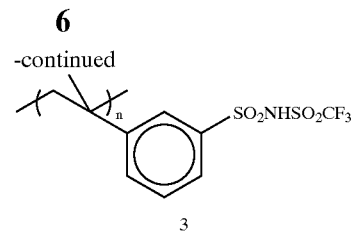

Polymethyl styrene (0.25 g)(obtained from Aldrich Chemical Co., Milwaukee, Wis.) was dissolved in 2.5 ml of dry $CCl_4$. To this was added 0.78 g of $CF_3SO_2NHSO_2Cl$ (sourced as above) and the resulting solution was heated to 80° C. under nitrogen. After about 15 minutes the solution became viscous and an additional 1 ml of $CCl_4$ was added. The solution was heated to 80° C. for an additional 2 hours and then the solvent was remove under vacuum. To the dried product was added 10 ml of water and it was allowed to stir overnight. The resulting white solid (0.34 g) was isolated by filtration and a portion was dissolved in 1 M NaOH in $D_2O$ for NMR analysis. Fluorine NMR showed a broad peak at $-74.7$ ppm due to the Na salt of the desired polymer (3) and a smaller, sharper peak at $-76.7$ ppm, attributed to $CF_3SO_2NH_2$ formed from hydrolysis of the starting acid by residual water.

Various modifications and alterations of this invention will become apparent to those skilled in the art without departing from the scope and principles of this invention, and it should be understood that this invention is not to be unduly limited to the illustrative embodiments set forth hereinabove. All publications and patents are herein incorporated by reference to the same extent as if each individual publication or patent was specifically and individually indicated to be incorporated by reference.

I claim:

1. A compound having pendant sulfonylimide groups according to formula (V):

$$(Ar-SO_2-)_m-QH-(-SO_2-R_1)_n \qquad (V)$$

wherein Ar is an aromatic group derived from an aromatic polymer;

wherein Q is N;

wherein each $R_1$ is independently selected from the group consisting of aliphatic and aromatic groups, which may or may not be saturated, unsaturated, straight-chain, branched, cyclic, heteroatomic, polymeric, halogenated, fluorinated or substituted;

wherein at least one $R_1$ contains at least one highly acidic group selected from the group consisting of: sulfonic acid, carboxylic acid and phosphonic acid;

wherein m is greater than 0;

wherein n is greater than 0;

wherein m+n=2 when Q is N; and wherein m+n=3 when Q is C.

2. A compound according to claim 1 wherein Q is N, m=1 and n=1.

3. A compound according to claim 1 wherein at least one $R_1$ contains at least one sulfonic acid group.

4. A compound according to claim 1 wherein $R_1$ comprises an aromatic group according to the formula: $-PhY_{5-v}(SO_2H)_v$;

wherein Ph is phenyl;

wherein each Y is independently selected from H, F, Cl and $CH_3$; and wherein v is 1, 2 or 3.

* * * * *

UNITED STATES PATENT AND TRADEMARK OFFICE
CERTIFICATE OF CORRECTION

PATENT NO. : 6,683,209 B2
DATED : January 27, 2004
INVENTOR(S) : Hamrock, Steven J.

It is certified that error appears in the above-identified patent and that said Letters Patent is hereby corrected as shown below:

Column 3,
Line 13, "Rmay be" should read -- $R_1$ may be --

Signed and Sealed this

Sixth Day of July, 2004

JON W. DUDAS
*Acting Director of the United States Patent and Trademark Office*